(12) United States Patent
Gill et al.

(10) Patent No.: US 8,523,539 B2
(45) Date of Patent: Sep. 3, 2013

(54) CENTRIFUGAL PUMP

(75) Inventors: Brijesh Gill, Houston, TX (US);
Charles S. Cox, Jr., Bellaire, TX (US);
Kevin R. Aroom, Houston, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 456 days.

(21) Appl. No.: 12/483,287

(22) Filed: Jun. 12, 2009

(65) Prior Publication Data
US 2009/0317271 A1 Dec. 24, 2009

Related U.S. Application Data

(60) Provisional application No. 61/074,053, filed on Jun. 19, 2008.

(51) Int. Cl.
*F04B 35/04* (2006.01)
*F16C 33/02* (2006.01)

(52) U.S. Cl.
USPC .......... 417/423.12; 384/280; 415/90

(58) Field of Classification Search
USPC ............ 417/420, 423.7, 423.12; 415/90; 384/276, 280, 295
See application file for complete search history.

(56) References Cited

U.S. PATENT DOCUMENTS

| | | | |
|---|---|---|---|
| 2,763,214 A | 9/1956 | White | |
| 2,782,721 A * | 2/1957 | White | 417/357 |
| 3,194,165 A * | 7/1965 | Sorlin | 417/353 |
| 3,802,804 A | 4/1974 | Zimmerman | |
| 3,932,069 A * | 1/1976 | Giardini et al. | 417/420 |
| 4,255,081 A | 3/1981 | Oklejas et al. | |
| 4,258,551 A | 3/1981 | Ritzi | |
| 4,304,532 A * | 12/1981 | McCoy | 417/420 |
| 4,422,809 A | 12/1983 | Bonin et al. | |
| 4,441,322 A | 4/1984 | Ritzi | |
| 4,634,344 A * | 1/1987 | Zagar et al. | 416/175 |
| 5,079,467 A * | 1/1992 | Dorman | 310/156.12 |
| 5,269,664 A * | 12/1993 | Buse | 417/360 |
| 5,332,374 A * | 7/1994 | Kricker et al. | 417/420 |
| 5,803,720 A * | 9/1998 | Ohara et al. | 417/420 |
| 6,100,618 A | 8/2000 | Schoeb et al. | |
| 6,183,220 B1 | 2/2001 | Ohara et al. | |
| 6,227,796 B1 | 5/2001 | Markovitch | |
| 6,375,412 B1 | 4/2002 | Dial | |
| 6,439,845 B1 * | 8/2002 | Veres | 415/206 |
| 6,506,012 B2 | 1/2003 | Tuck, Jr. | |
| 6,736,768 B2 | 5/2004 | Felt et al. | |
| 6,776,575 B2 | 8/2004 | Tuck, Jr. | |
| 7,094,196 B2 | 8/2006 | Felt et al. | |
| 7,192,244 B2 | 3/2007 | Grande, III et al. | |
| 7,341,424 B2 | 3/2008 | Dial | |
| 7,400,052 B1 | 7/2008 | Badger | |
| 7,425,807 B1 | 9/2008 | Perkins et al. | |
| 2003/0118461 A1* | 6/2003 | Hodapp et al. | 417/423.7 |
| 2003/0135086 A1 | 7/2003 | Khaw et al. | |
| 2007/0280841 A1 | 12/2007 | LaRose et al. | |

* cited by examiner

*Primary Examiner* — Peter J Bertheaud
(74) *Attorney, Agent, or Firm* — Streets & Steele

(57) ABSTRACT

The invention is directed to a multi-disk centrifugal pump suitable for pumping fluids, including biocompatible fluids, such as blood. The design of the pump components is optimized to reduce or eliminate the probability of clotting and hemolysis when pumping blood, and to be energy efficient and resistant to physical shock for portable applications.

15 Claims, 8 Drawing Sheets

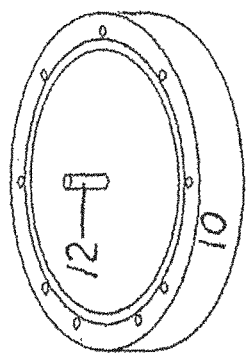
Fig. 1d
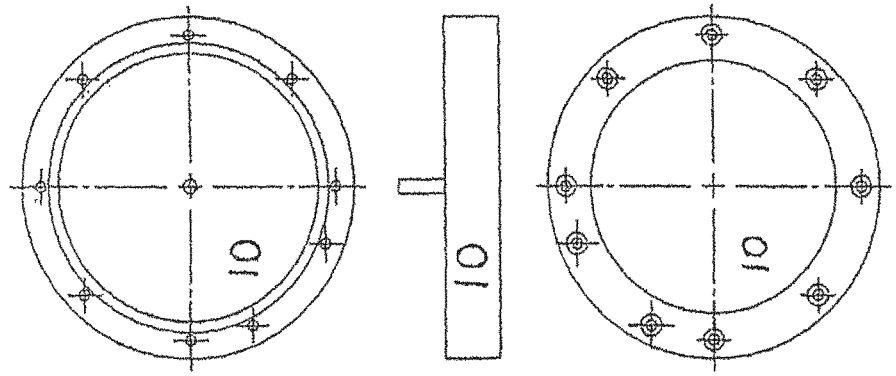
Fig. 1a
Fig. 1b
Fig. 1c

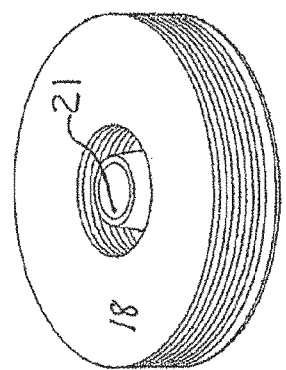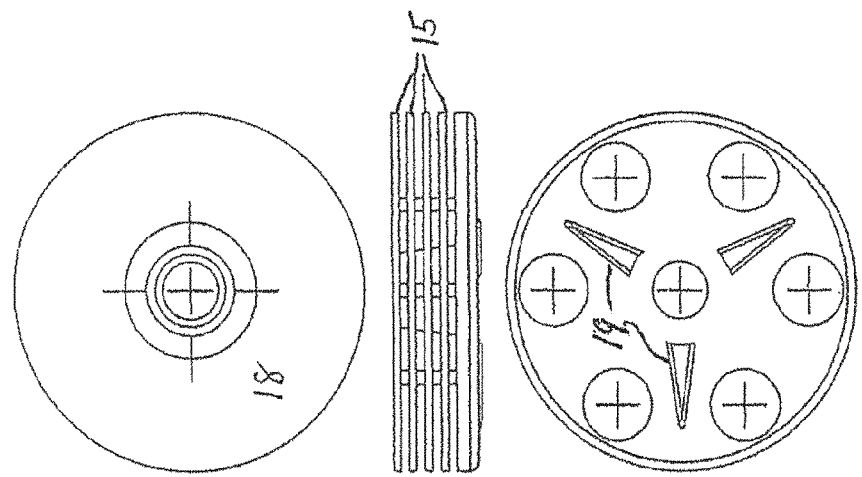

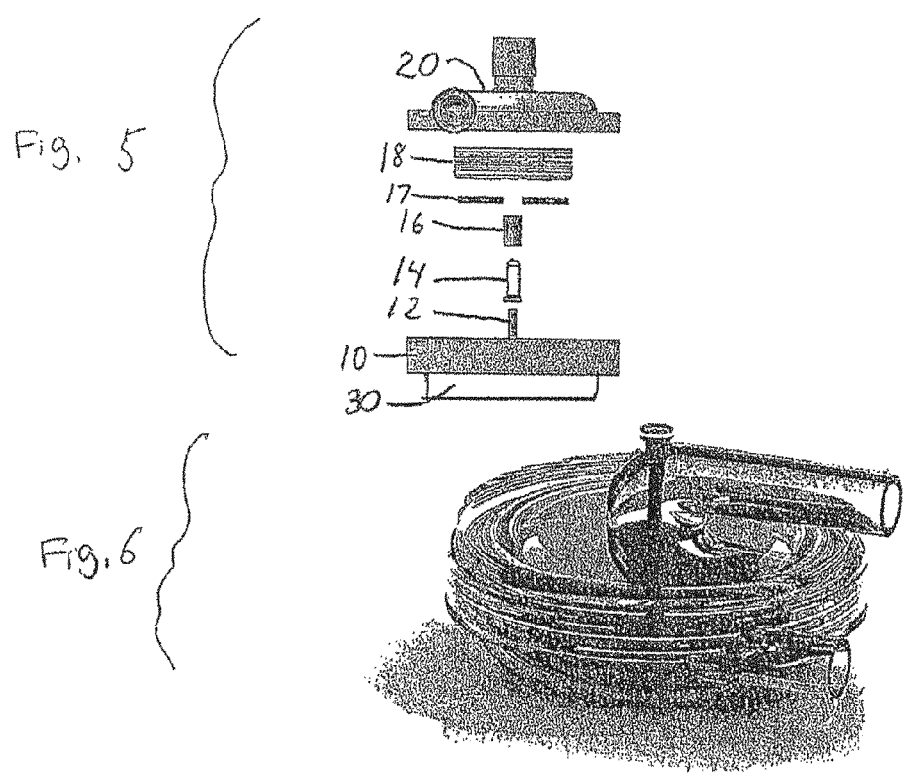

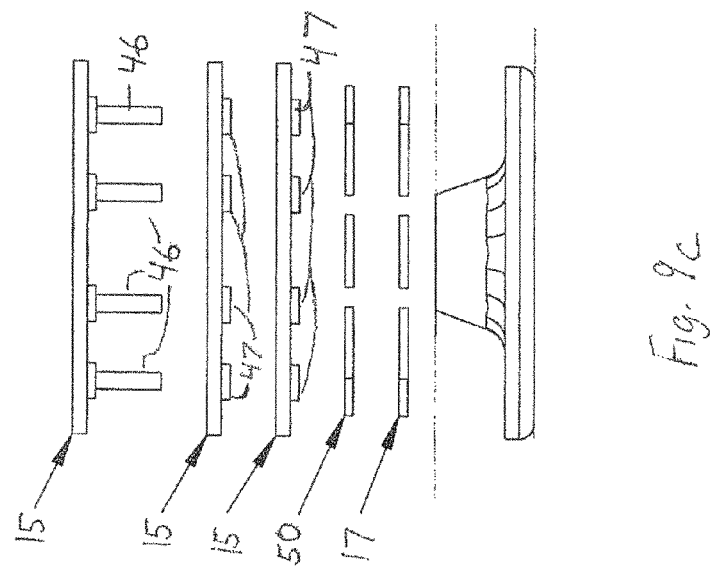
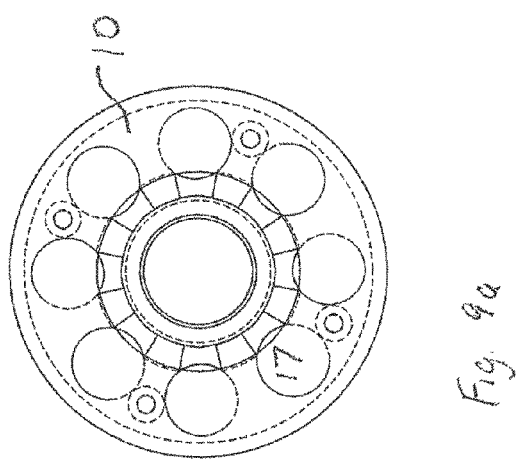
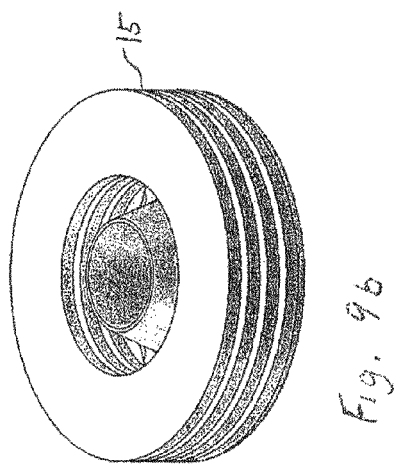

CENTRIFUGAL PUMP

PRIORITY INFORMATION

This application claims the benefit of U.S. Provisional Application No. 61/074,053, filed on Jun. 19, 2008.

GOVERNMENT RIGHTS

This invention was made with United States Government support under Grant No. W81XWH-07-1-0496, awarded by the United States Army. The United States Government has certain rights in the invention.

FIELD OF THE INVENTION

The invention is directed to a multi-disk centrifugal pump suitable for pumping fluids, including biocompatible fluids, such as blood. The design of the pump components is optimized to reduce or eliminate the probability of clotting and hemolysis when pumping blood, and to be energy efficient and resistant to physical shock for portable applications.

BACKGROUND OF THE INVENTION

Existing centrifugal blood pumps are large and waste electrical energy. Accordingly, they are not well suited for portable use. Existing ventricular assist devices ("VADs") do not scale down in size so that they can not be used in the pediatric application. These pumps have elaborate configurations of the inlet and outlet geometries to reduce turbulence, in order to provide high flow at acceptable rates of hemolysis. These complex features, when scaled down in size, no longer act to reduce turbulence but instead act to increase shear forces. The inlet and outlet of this pump design have a wide, continuous (uninterrupted) cross section without complex surface features, allowing the pump to be scaled down in size while still retaining acceptable performance

DETAILED DESCRIPTION OF THE DRAWINGS

FIG. 1a is a top view of the bottom housing of a preferred embodiment of the invention.

FIG. 1b is a side view of the bottom housing of a preferred embodiment of the invention.

FIG. 1c is a bottom view of the bottom housing of a preferred embodiment of the invention.

FIG. 1d is an isometric view of the bottom housing of a preferred embodiment of the invention.

FIG. 4a is a top view of the rotor of a preferred embodiment of the invention.

FIG. 4b is a side view of the rotor of a preferred embodiment of the invention.

FIG. 4c is a bottom view of the rotor of a preferred embodiment of the invention.

FIG. 4d is an isometric view of the rotor of a preferred embodiment of the invention.

FIG. 5 is an exploded side view of a preferred embodiment of the invention.

FIG. 6 is a side view of a preferred embodiment of the invention.

FIG. 7b is a bottom view of the single piece rotor shown in FIG. 7a.

FIG. 7c is an isometric view of the single piece rotor shown in FIG. 7a.

FIG. 8 is a side cross sectional view of the embodiment of the invention shown in FIG. 8a.

FIG. 9a is a bottom view of another embodiment of a rotor suitable for use with the present invention.

FIG. 9b is an isometric view of the rotor shown in FIG. 9a.

FIG. 9c is an exploded side view of the rotor shown in FIG. 9a.

DETAILED DESCRIPTION OF THE PREFERRED EMBODIMENTS

A preferred embodiment of the invention is directed to a Tesla centrifugal pump for pumping biocompatible fluids, such a blood. In one preferred embodiment, the pump is made from biocompatible materials, thereby making it suitable for implantation in a patient, including in a human patient. In another preferred embodiment, the pump is made from non-biocompatible materials and coated with a biocompatible material coating. The Tesla design was chosen because it creates less turbulence and is less susceptible to cavitation than traditional bladed centrifugal pumps. Therefore, the Tesla design should produce less hemolysis. Additionally, the bladeless geometry of the Tesla impeller allows the design to be scaled down in size while less susceptible to performance variability from the dominance of viscous forces at a small scale.

A preferred embodiment of the invention comprises a pump housing bottom 10, as shown in FIGS. 1a-1d, 7b and 9a. In a preferred embodiment, the pump housing bottom is circular. A preferred embodiment of the invention comprises a post 12 located in the center of the top surface of the pump housing bottom and protruding outward. The post defines a longitudinal axis. In a preferred embodiment, the post is integrally formed with the pump housing bottom. In a preferred embodiment, the pump housing bottom is made from a biocompatible material.

Figure 2D:
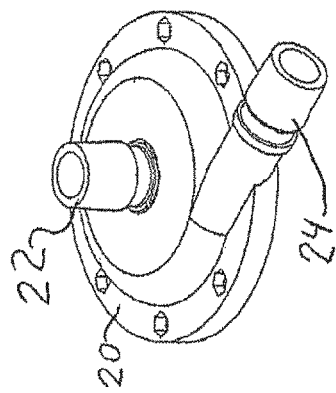
FIG. 2d is an isometric view of the top housing of a preferred embodiment of the invention.
Figures 2A, 2B, 2C:
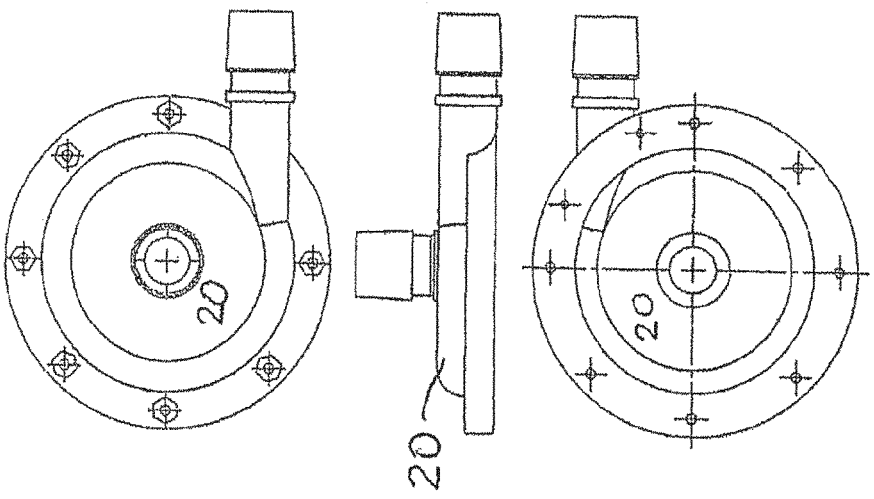
FIG. 2a is a top view of the top housing of a preferred embodiment of the invention.
FIG. 2b is a side view of the top housing of a preferred embodiment of the invention.
FIG. 2c is a bottom view of the top housing of a preferred embodiment of the invention.
Figure 3:
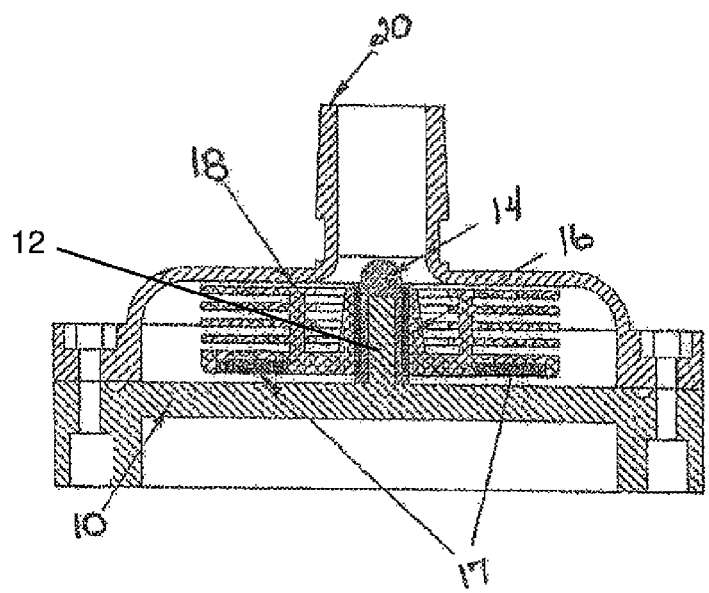
FIG. 3 is a cross sectional view of a preferred embodiment of the invention.

A preferred embodiment of the invention further comprises a first sheath 14 mounted over the post 12, as shown in FIGS. 3 and 5. In a preferred embodiment, the first sheath is made from a flurocarbon polymer, such as polytetrafluoroethylene ("PTFE"). In a preferred embodiment, the invention further comprises a second sheath 16 mounted over the first sheath, as shown in FIG. 3. In a preferred embodiment, the second sheath is made from stainless steel. In a preferred embodiment, the first sheath comprises a thrust bearing.

Figure 8:
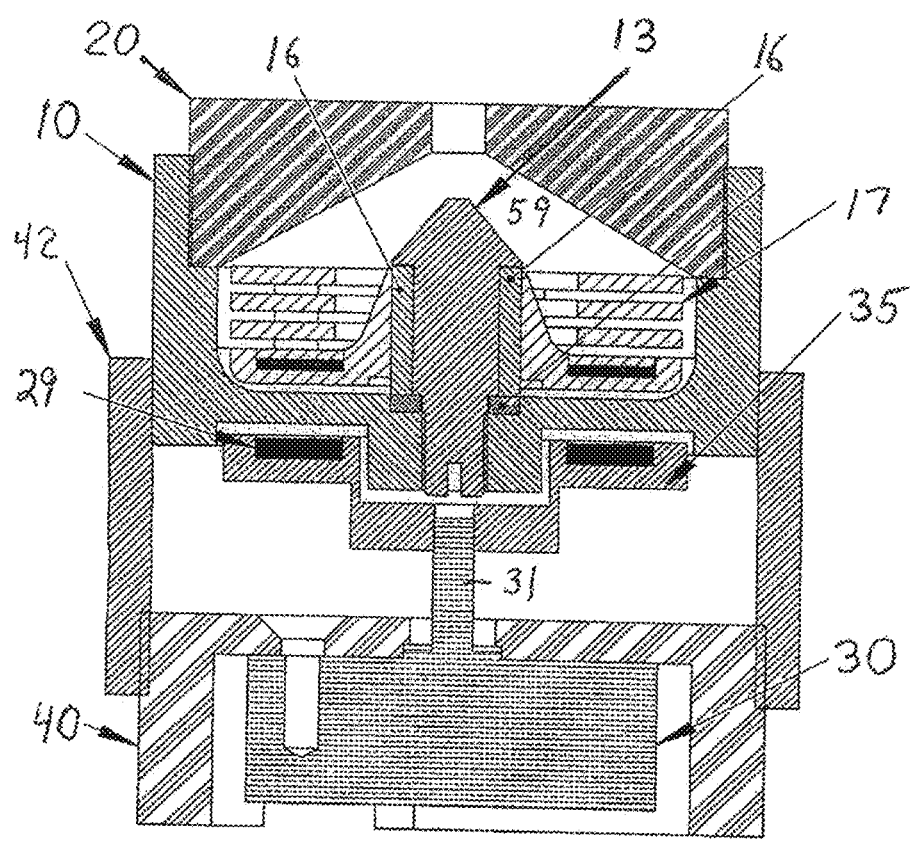

A preferred embodiment of the invention further comprises a pump housing top 20, as shown in FIGS. 2a-2d. The pump housing top and bottom collectively form the pump housing, In a preferred embodiment, the pump housing top is circular. In another preferred embodiment, as shown in FIG. 8, the pump housing top comprises a conically shaped interior 59. This conically shaped interior reduces the rapid acceleration of fluid as it enters this pump.

The pump housing top comprises an inlet conduit 22 centrally located in the pump housing. As shown in FIG. 5, the pump housing top is mounted on the pump housing bottom to form the pump housing. In a preferred embodiment, the inlet conduit is oriented in substantial alignment with the longitudinal axis. In another preferred embodiment, the inlet conduit is centered over the post. In a preferred embodiment, no vanes or diffusers are present inside the inlet conduit. In a preferred embodiment, the inlet conduit permits fluid to enter the housing along an axis that is substantially parallel to the longitudinal axis. In a preferred embodiment, the inlet conduit 22 is circular.

The pump housing top further comprises an outlet conduit 24 located in an outer radial region of the pump housing. In a preferred embodiment, the outlet can be integrally formed as part of the pump housing bottom. In a preferred embodiment, the outlet conduit 24 is circular. In another preferred embodiment, the orientation of the inlet conduit is substantially perpendicular to the orientation of the outlet conduit. In another preferred embodiment, the outlet conduit extends beyond the outer radial edge of the pump housing top. In a preferred embodiment, the pump housing top is made from a biocompatible material. In a preferred embodiment, the inlet conduit and the outlet conduit are integrally formed in the pump housing top.

A preferred embodiment of the invention further comprises a rotatably mounted pump rotor, 18, as shown in FIGS. 3 and 4a-4d. The rotor design used in a preferred embodiment of the invention is commonly known in the centrifugal pump arts as a "Tesla" design. In a preferred embodiment, the rotor comprises multiple disks 15 stacked in a longitudinally aligned configuration as shown in FIGS. 3 and 4d. In a preferred embodiment, the rotor comprises four disks. In a preferred embodiment, the rotor is made from a polycarbonate material. In a preferred embodiment, the rotor comprises a central channel 21, as shown in FIG. 4d. As shown in FIG. 3, the rotor is positioned such that the second sheath 16 protrudes through the central channel.

In a preferred embodiment, a cap 13 is mounted on the top central region of the rotor, as shown in FIG. 8. The cap holds the rotor in a fixed axial position, thereby preventing lift and subsequent decoupling.

Figure 7B:
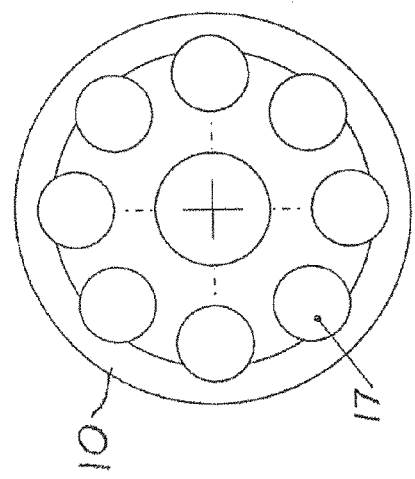
Figure 7A:
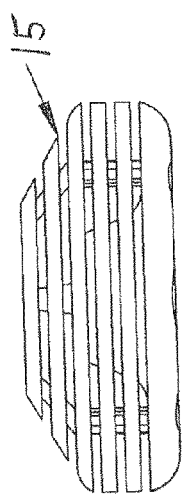
FIG. 7a is a side view of a single piece rotor suitable for use with the present invention.
Figure 7C:
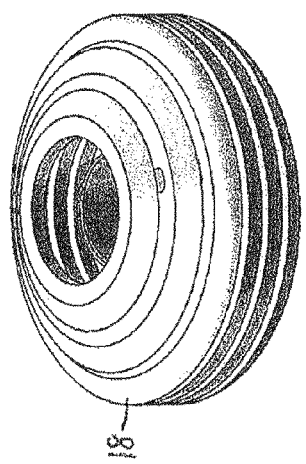

In one preferred embodiment, the rotor disk diameters are substantially equivalent to each other, as shown in FIG. 4b. In another preferred embodiment, the top rotor disk has a smaller diameter than all rotor disks below it and the second rotor disk from the top has a smaller diameter than all rotor disks below it, as shown in FIG. 7a. In this embodiment, the outer edges of the top three rotor discs are beveled, as shown in FIG. 7a. The embodiment of the invention shown in FIGS. 7a and 7c provides a more gradual acceleration of the fluid in the pump, than does the embodiment shown in FIG. 4b. This more gradual acceleration reduces the shear forces caused by elevated velocity gradients.

The term "third of said disk" is used herein to refer to a one third slice of a disk extending from the radial center to the disk to the outer periphery of the disk and comprising a 120 degree arc length of the disk. In another preferred embodiment, the top disk has at least two diametrically opposed studs 46 protruding downward and each remaining disk comprises at least one hole aligned with and positioned to receive each stud, thereby aligning all of the disks, as shown in FIG. 9c. In another preferred embodiment, each disk comprises at least three spacers 47, each positioned in a separate third of said disk, as shown in FIG. 9c.

In a preferred embodiment, the spacing between each disk is greater than or equal to 0.02". In a preferred embodiment, it is desirable to make the disks as thin as possible, while maintaining the desired structural integrity for pumping biocompatible fluids. In a preferred embodiment, the disk thickness is greater than or equal to 0.03". Thinner disks allow for greater total surface area of the rotor at the cost of reducing the strength of the disks and increasing the risk of vibration or breakage. A larger moment of inertia would require more energy to turn, hence reducing motor battery life. For pumps of constant overall volute volume, thicker disks reduce overall priming volume of the pump.

In one preferred embodiment, the disks are integrally formed as one piece of the pump, as shown in FIG. 7a. This one piece or "monolithic" construction provides increased strength to the rotor. This monolithic construction also avoids the vibration or jitter problems associated with multipiece stacked rotor designs of prior art Tesla centrifugal pumps. Such mechanical vibration is particularly undesirable in a pump intended to pump biocompatible fluids, such as blood, because higher rates of hemolysis are produced and energy consumption is increased. Additionally, the monolithic construction is more resistant to external forces, including random vibrations and shocks, than a multipiece rotor design. This attribute further reduces the probability of hemolysis when pumping blood with this pump.

In a preferred embodiment, the rotor has an outer diameter that is less than 1.75", and an inner diameter that is less than 1.25". In another preferred embodiment, the inner diameter is at least 0.7" and the outer diameter is at least 1.3".

In order to eliminate the need to create a shaft seal for power transfer, a preferred embodiment of the invention comprises a magnetic coupling system. In a preferred embodiment, this coupling comprises a first set of magnets, comprising an even number of magnets 17 embedded in the bottom of the rotor in a circular fashion or arrangement. In another preferred embodiment, the first set of magnets comprises two magnets embedded in the bottom of the rotor, as shown in FIG. 3. In a preferred embodiment, each of the magnets in a set is substantially equal in mass to each of the other magnets in the set. In another preferred embodiment, the first set of magnets contains eight magnets, and the rotor bottom is configured to hold eight magnets, as shown in FIGS. 7b and 9a. In another preferred embodiment, the magnets are sealed with a cap 50 in the bottom of the rotor, as shown in FIG. 9c.

In a preferred embodiment, a second set of magnets 29 identical in number and geometry to the first set is operatively coupled to a motor 30 located outside the pump housing, as shown in FIG. 8. In a preferred embodiment, the motor is located in a motor housing 40, as shown in FIG. 8. In a preferred embodiment, the motor housing is connected to the bottom housing by a coupler 42, as shown in FIG. 8. In a preferred embodiment, the motor comprises a shaft 31 that is coupled to the second set of magnets, such that rotation of the shaft causes rotation of the second set of magnets, as shown in FIG. 8. In a preferred embodiment, the shaft comprises at least two fins.

In a preferred embodiment, the second set of magnets are mounted in a magnet housing 35, as shown in FIG. 8. The magnets of opposite polarity are attracted to each other, and one set of magnets tries to maintain its position relative to the other set, creating a magnetic coupling through the housing. This coupling provides effective torque transfer to the rotor. This design eliminates the need for a shaft seal. In a preferred embodiment, the motor is battery powered. In another preferred embodiment, the motor is a DC flat motor.

In a preferred embodiment, this pump is not designed to replace the cardiac output capacity of an adult's heart. Such high flow requirements would demand power levels that are neither suitable nor necessary for mobile use. In one embodiment, a target flow rate for this pump is approximately 1 L/min at a pressure head of 120 mm Hg.

In a preferred embodiment, the rotor further comprises at least two washout fins 19 on the bottom of the rotor, as shown in FIG. 4c. These washout fins keep pumped fluid moving in an area where it could otherwise become stagnant and begin to clot.

In a preferred embodiment, the central bearing is quite wide by comparison to other pump designs. This allows external perturbing forces to be distributed across a much larger area than with other pumps, giving greater resistance to external shock/vibration. The cross section of the overall central spindle is a segment of a cone (frustum) with the smaller diameter pointed into the inlet stream. This allows both a more gradual acceleration of the fluid and less resistance to flow through the inlet, reducing the overall pressure drop across the pump and reducing hemolysis.

Those skilled in the art of pumping blood will appreciate that a tradeoff occurs in the design of a blood pump between keeping the fluid moving to reduce the chances of clot (thrombus) formation within the pump. It is important to avoid introducing areas of excessive shear rate that can cause the destruction of red blood cells (hemolysis). This tradeoff manifests itself in the design process through selecting proper clearances between the rotor and the housing.

The differences in centrifugal pump disk support structure design lie in the location and shape of the support. The tradeoff between hemolysis and thrombosis is important. Disk supports that are too close to the center of the rotor could produce eddies where stagnation could occur, causing thrombi formation. Alternatively a set of disk supports on the outermost edge may create an unacceptably high level of trauma to blood cells due to the increased velocity present at the outer radii of the disks. A teardrop shaped disk support structure that is narrow near the center and widens as it moves radially outward acts as an effective shape that eliminates areas of stagnation while allowing smooth movement around it, limiting both hemolysis and thrombosis.

An important design criterion for a pediatric ventricular assist device ("VAD") is the priming volume of the device, which cannot use a significant percentage of the infant's overall blood volume simply to fill up the pump. In a preferred embodiment, this pump minimizes priming volumes in two ways: first, the inter-disc spacing is reduced to just above the point where hemolysis begins to increase (~1 mm, a function of blood viscosity and surface roughness of the rotor). In a preferred embodiment, the overall rotor is elevated off the bottom of the housing in order to prevent excessive hemolysis. In another preferred embodiment, the fluid encounters disks of successively increasing diameter, as it flows from inlet to outlet, as shown in FIG. 7.

The foregoing disclosure and description of the inventions are illustrative and explanatory. Various changes in the size, shape, and materials, as well as in the details of the illustrative construction and/or an illustrative method may be made without departing from the spirit of the invention.

What is claimed is:

1. A centrifugal pump comprising:
   a. a pump housing bottom comprising a top surface;
   b. a post located in the center of the top surface of the pump housing bottom and protruding outward to define a longitudinal axis;
   c. a first sleeve-shaped sheath mounted circumferentially about the post;
   d. a second sleeve-shaped sheath mounted circumferentially about the post and over the first sheath;
   e. a pump housing top mounted on the pump housing bottom, wherein said pump housing top and bottom collectively form the pump housing, and comprising an inlet conduit centrally located in the pump housing;
   f. an outlet conduit located in an outer radial region of the pump housing;
   g. a monolithic, rotatably mounted and bladeless pump rotor rotatable with the second sheath and comprising a central channel positioned such that the first sheath resides within the central channel, a plurality of stacked disks each extending radially outward from the central channel, and a frustoconical portion intermediate the stacked disks and the inlet conduit of the pump housing, the frustoconical portion having a base diameter proximal the stacked disks and an inlet diameter proximal to the inlet conduit;
   h. a first set of magnets, comprising an even number of magnets, embedded in the bottom of the rotor; and
   i. a second set of magnets comprising the same number of magnets as the first set of magnets mounted outside the pump housing;
   wherein the second sheath extends substantially the length of the central channel of the pump rotor to prevent the central channel of the pump rotor from contacting the first sheath mounted about the post;
   wherein the frustoconical portion of the rotatably mounted pump rotor is aligned with the inlet conduit; and
   wherein the frustoconical portion of the rotatably mounted pump rotor diverts a fluid entering the pump housing from the inlet conduit radially outwardly onto the stacked disks of the rotatably mounted pump rotor to substantially decrease a magnitude of acceleration imparted to the fluid by the stacked disks.

2. The centrifugal pump of claim 1, wherein the post is integrally formed with the pump housing bottom.

3. The centrifugal pump of claim 1, wherein the pump housing bottom is made from a biocompatible material.

4. The centrifugal pump of claim 1, wherein the first sheath is made from a fluorocarbon polymer.

5. The centrifugal pump of claim 1, wherein the second sheath is made from stainless steel.

6. The centrifugal pump of claim 1, wherein the inlet conduit is oriented in substantial alignment with the longitudinal axis.

7. The centrifugal pump of claim 1, wherein the inlet conduit is centered over the post.

8. The centrifugal pump of claim 1, wherein the orientation of the inlet conduit is substantially perpendicular to the orientation of the outlet conduit.

9. The centrifugal pump of claim 1, wherein the inlet conduit and the outlet conduit are integrally formed in the pump housing top.

10. The centrifugal pump of claim 1, wherein the rotor is a monolithic and unitary structure made from a polycarbonate material.

11. The centrifugal pump of claim 1, wherein a spacing between two adjacent ones of the plurality of disks is at least 0.02 inches.

12. The centrifugal pump of claim 1, wherein each of the plurality of disks has a thickness of at least 0.03 inches.

13. The centrifugal pump of claim 1, wherein the rotor comprises at least two washout fins disposed on the rotor at a position generally opposite the stacked disks from the frustoconical portion.

14. The centrifugal pump of claim 1, further comprising a plurality of washout fins mounted on a bottom of the rotor proximal to the pump housing bottom.

15. A centrifugal pump comprising:
   a. a pump housing bottom comprising a top surface;

b. a post located in the center of the top surface of the pump housing bottom and protruding outward to define a longitudinal axis;
c. a first sleeve-shaped sheath mounted circumferentially about the post;
d. a second sleeve-shaped sheath mounted circumferentially about the post and over the first sheath;
e. a pump housing top mounted on the pump housing bottom, wherein said pump housing top and bottom collectively form the pump housing, and comprising an inlet conduit centrally located in the pump housing;
f. an outlet conduit located in an outer radial region of the pump housing;
g. a monolithic, rotatably mounted and bladeless pump rotor rotatable with the second sheath and comprising a central channel positioned such that the first sheath resides within the central channel and a plurality of stacked disks each extending radially outward from the central channel, and each stacked disk having an internal diameter and an external diameter such that the internal diameter is larger than a diameter of the inlet conduit and also at least 40% of the external diameter;
h. a first set of magnets, comprising an even number of magnets, embedded in the bottom of the rotor; and
i. a second set of magnets comprising the same number of magnets as the first set of magnets mounted outside the pump housing
wherein the second sheath extends substantially the length of the central channel of the pump rotor to prevent the central channel of the pump rotor from contacting the first sheath mounted about the post.

* * * * *